(12) United States Patent
Jackson et al.

(10) Patent No.: US 12,334,199 B2
(45) Date of Patent: Jun. 17, 2025

(54) AUTOMATED TRANSFORMATION DOCUMENTATION OF MEDICAL DATA

(71) Applicant: CERNER INNOVATION, INC., Kansas City, KS (US)

(72) Inventors: Margaret M. Jackson, Collegeville, PA (US); Peter Teunissen, Kansas City, KS (US); Andres Hernandez, Kansas City, KS (US); Steven Ger, Kansas City, KS (US); Daniel Holder, Kansas City, KS (US); Mark L. Smith, Lee's Summit, MO (US)

(73) Assignee: Cerner Innovation, Inc., Kansas City, MO (US)

( * ) Notice: Subject to any disclaimer, the term of this patent is extended or adjusted under 35 U.S.C. 154(b) by 416 days.

(21) Appl. No.: 17/497,324

(22) Filed: Oct. 8, 2021

(65) Prior Publication Data

US 2022/0189596 A1  Jun. 16, 2022

Related U.S. Application Data

(60) Provisional application No. 63/123,850, filed on Dec. 10, 2020.

(51) Int. Cl.
| | |
|---|---|
| *G16H 15/00* | (2018.01) |
| *G06F 16/215* | (2019.01) |
| *G06F 16/25* | (2019.01) |
| *G16H 10/60* | (2018.01) |

(52) U.S. Cl.
CPC .......... *G16H 15/00* (2018.01); *G06F 16/215* (2019.01); *G06F 16/256* (2019.01); *G16H 10/60* (2018.01)

(58) Field of Classification Search
CPC ...... G16H 15/00; G16H 10/60; G06F 16/215; G06F 16/256
See application file for complete search history.

(56) References Cited

U.S. PATENT DOCUMENTS

| | | | | |
|---|---|---|---|---|
| 8,495,069 | B2* | 7/2013 | Friedlander | G16Z 99/00 |
| | | | | 707/748 |
| 8,898,798 | B2* | 11/2014 | Rogers | G06Q 10/10 |
| | | | | 726/28 |
| 2016/0210427 | A1* | 7/2016 | Mynhier | G16H 10/60 |
| 2017/0091388 | A1* | 3/2017 | Zolla | G16H 10/60 |
| 2019/0384849 | A1* | 12/2019 | Sundararaman | G16H 30/20 |
| 2020/0335188 | A1* | 10/2020 | Ozeran | G16H 40/63 |

* cited by examiner

*Primary Examiner* — Sheetal R Paulson
(74) *Attorney, Agent, or Firm* — Invoke

(57) ABSTRACT

Systems, methods, and storage media useful in a healthcare cloud computing platform to transform, deduplicate and store medical data from third-party databases to a patient's primary medical record in the healthcare cloud computing platform. Exemplary implementations may: load and read data from third-party databases, and determine if it is duplicative of what is in the patient's primary record. Other embodiments, provide a method for ranking medical data from two different third-party databases to determine which medical data should be written to the patient's primary medical record in the healthcare computing platform.

20 Claims, 10 Drawing Sheets

300

STATE TRANSITION MANAGER AND RULES

| | PATIENT | CODING | TEXT | DATE ONSET | RULES DUPLICATE |
|---|---|---|---|---|---|
| RECORD 1 HIE 1 | T | T | F | T | |
| RECORD 2 EMR 1 | T | T | T | T | =F |
| RECORD 3 EMR 2 | T | T | T | T | |
| RECORD 4 EMR 1 | T | T | T | T | =T |

*FIG. 3.*

| RULE WEIGHT: | Rule-1 0.33 | | Rule-2 0.33 | | Rule-3 0.33 | | | outcome |
|---|---|---|---|---|---|---|---|---|
| | ONSETDTIME | | CLINICALSTATUS | | VERIFICATIONSTATUS | | sum | |
| | COMPARATOR= OLDEST WINS | WINNER=1 LOSER=0 | ENUM ORDER AND FACTOR: RESOLVED=1, FACTOR=1.0 INACTIVE=2, FACTOR=0.75 ACTIVE=3, FACTOR=0.5 NULL=4, FACTOR=0.25 | | ENUM ORDER AND FACTOR: ENTERED-IN-ERROR=1, FACTOR=1.0 REFUTED=2, FACTOR=0.75 CONFIRMED=3, FACTOR=0.5 UNCONFIRMED=4, FACTOR=0.25 NULL=5, FACTOR= | | | |
| ALLERGY-1 | 1/1/2020 | 0X0.33=0 | RESOLVED | 1X0.33=.033 | ENTER-IN-ERROR | 1X0.33=.033 | 0.66 | WINNER |
| ALLERGY-2 | 1/1/2020 | 1X0.33=0.33 | ACTIVE | 0.5X0.33=0.165 | UNCONFIRMED | 0.25X0.33=0.0825 | 0.5775 | LOSER |
| ALLERGY-3 | 1/1/2020 | 1X0.33=0.33 | RESOLVED | 1X0.33=0.33 | REFUTED | 0.75X0.33=0.2475 | 0.9075 | TIE" MOVE ON TO NEXT CRITERIA |
| ALLERGY-4 | 1/1/2020 | 1X0.33=0.33 | ACTIVE | 0.75X0.33=0.2475 | ENTER-IN-ERROR | 1X0.33=.033 | 0.9075 | TIE" MOVE ON TO NEXT CRITERIA |
| ALLERGY-10 | 1/1/2020 | 1X0.33=0.33 | RESOLVED | 1X0.33=0.33 | CONFIRMED | 0.5X0.33=0.165 | 0.825 | TIE" MOVE ON TO NEXT CRITERIA |
| ALLERGY-20 | 1/1/2020 | 1X0.33=0.33 | ACTIVE | 0.5X0.33=0.165 | ENTERED-IN-ERROR | 1X0.33=.033 | 0.825 | TIE" MOVE ON TO NEXT CRITERIA |

FIG. 6.

|  | RULE-1 |  |  |  |
|---|---|---|---|---|
| RULE WEIGHT: | 1.0 |  |  |  |
|  | ONSETDTIME |  | SUM | RANKING OUTCOME |
|  | COMPARATOR='OLDEST WINS' |  |  |  |
|  |  |  |  |  |
| ALLERGY-1 | 1/1/2020 | 1X1.0=0.0 | 1.0 | WINNER |
| ALLERGY-2 | 1/1/2020 | 0X1.0=0.0 | 0.0 | LOSER |
|  |  |  |  |  |
| ALLERGY-3 | 1/1/2020 | 1X1.0=1.0 | 1.0 | TIE: MOVE ON TO NEXT CRITERIA |
| ALLERGY-4 | 1/1/2020 | 1X1.0=1.0 | 1.0 | TIE: MOVE ON TO NEXT CRITERIA |

```
1   CLASS: ORG.HL7.FHIR.R4.MODEL.ENCOUNTER
2   GROUPS:
3    - ID: 0
4      PROPERTIES:
5       - NAME: IDENTIFIER
6         COMPARATOR: LISTONEMATCH
7         PROPERTIES:
8          - NAME: VALUE
9          - NAME: SYSTEM
10         - NAME: TYPE.CODING
11           COMPARATOR: LISTONEMATCH
12           PROPERTIES:
13            - NAME: CODE
14        - NAME: SERVICEPROVIDER.REFERENCE
15   - ID: 1
16     PROPERTIES:
17      - NAME: CLASS_.CODE
18      - NAME: CLASS_.SYSTEM
19      - NAME: PERIOD.START
20      - NAME: PERIOD.END
```

*FIG. 9.*

AUTOMATED TRANSFORMATION DOCUMENTATION OF MEDICAL DATA

CROSS-REFERENCE TO RELATED APPLICATIONS AND PRIORITY CLAIM

This application claims the benefit of U.S. Provisional Patent Application No. 63/123,850, filed Dec. 10 2020, the entire contents of which is incorporated herein by reference.

BACKGROUND

Provider and clinician burden is an ongoing issue across healthcare. Clinical data is being captured within more and more sources system. Clinicians are unable to access information from multiple sources when treating a patient. Clinicians have an incomplete picture of a patient's health history when utilizing a conventional electronic medical record. Third-party databases contain information for the patient not in the patient's conventional electronic medical record that is maintained with a single healthcare system or electronic health records (EHR) vendor.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present disclosure is defined by the claims as supported by the Specification, including the Detailed Description.

Embodiments of the present invention improve implementation and on-going costs of maintaining patient data from multiple disparate sources. Embodiments of the present invention allow medical data for an individual patient to be maintained in a cloud environment and allows for the scaling of the data on a national and international scale rather than patient data being maintained in separate, disparate databases and electronic health records.

Embodiments of the present invention are not limited to location and demographics of patients. Additionally, embodiments allow for consistent implementation and storage of accurate, non-duplicative medical data from multiple databases for individual patients in single longitudinal record for the individual patient maintained in a healthcare cloud computing environment.

Embodiments of the present invention allow for clinicians to retrieve and view the most up-to-date information for a patient being treated regardless of the EMR system being utilized. Embodiments of the present invention identify other venues of care and third-party databases as "trusted sources". This allows for a flexible and elastic healthcare cloud computing platform that can be built to designate discrete clinical concepts to auto-write into the medical data being viewed for the individual patient, increasing efficiency and decreasing time spent by a clinician reviewing information.

In one embodiment, the aggregated and non-duplicative patient data is presented to providers and clinicians within their normal workflow, broken out by clinical concept. Medical data for patient(s) is auto-written and reconciled and resides within the record as discrete data retaining original author and source.

Medical data is presented to providers and clinicians within their normal workflow, broken out by clinical concept. The healthcare cloud computing platform includes medical data for individual patients across various internal and external sources giving a more complete view of an individual's health record. Embodiments of the present invention allow these large amounts of data to be normalized, deduplicated, ranked and written into the patient's primary record in seconds to minutes rather than taking days and weeks to collect and input into a patient's primary record.

BRIEF DESCRIPTION OF THE DRAWINGS

Illustrative aspects of the present invention are described in detail below with reference to the attached drawing figures, and wherein:

FIG. 3 depicts an exemplary state manager and duplication rules in accordance with an embodiment of the present invention.

FIG. 6 depicts an example of ranking rules in accordance with an embodiment of the present invention.

FIG. 7 depicts an example of ranking in accordance with an embodiment of the present invention.

FIG. 8 depicts exemplary Fast Healthcare Interoperability Resources (FHIR) under the HL7 standards in accordance with an embodiment of the present invention.

FIG. 9 depicts exemplary multiple medical properties in accordance with an embodiment of the present invention.

DETAILED DESCRIPTION

Figure 1A:
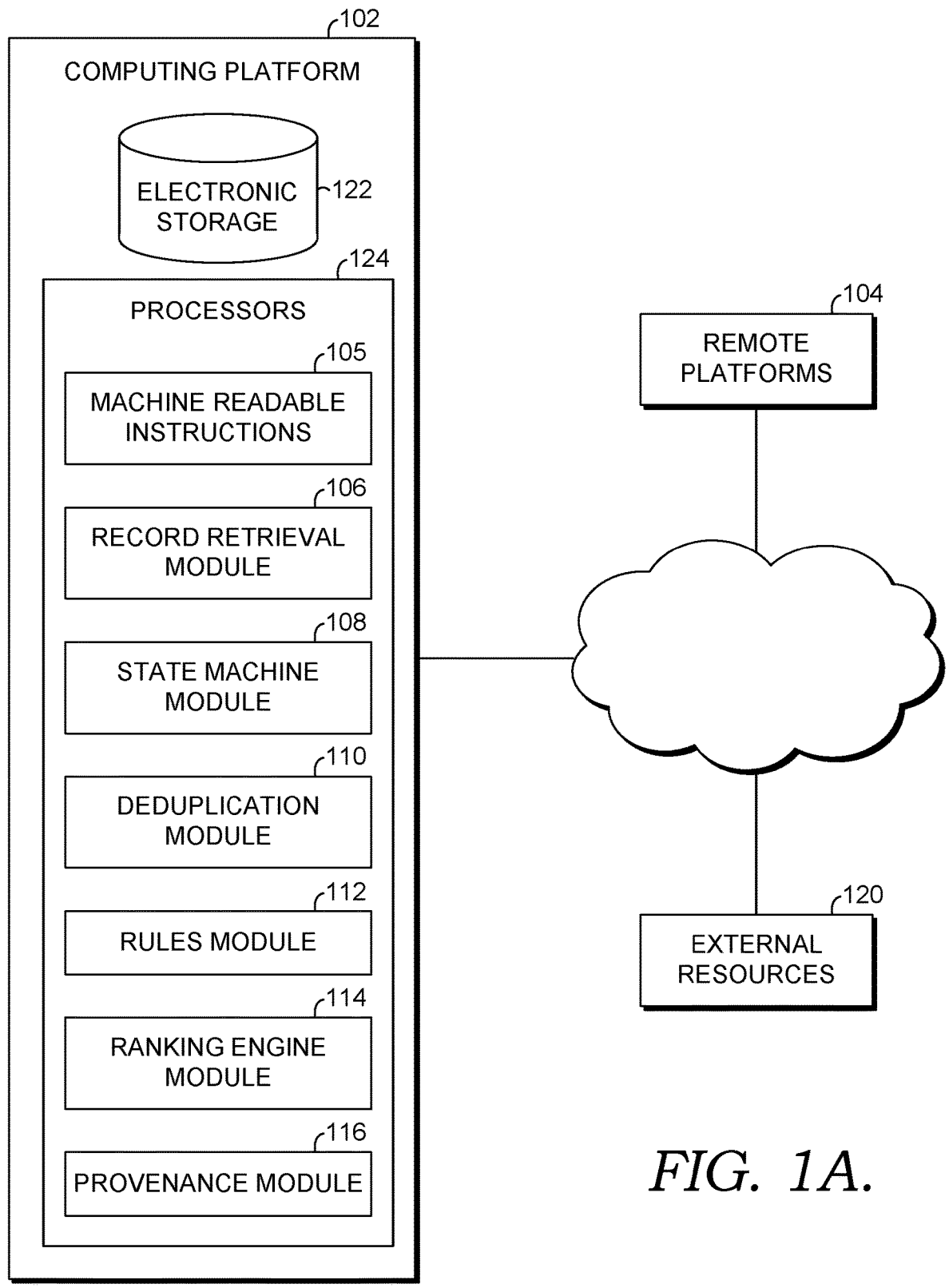
FIGS. 1A and 1B illustrates a healthcare cloud computing platform, in accordance with aspects.

The subject matter of the present invention is being described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Terms should not be interpreted as implying any particular order among or between various steps herein disclosed unless and except when the order of individual steps is explicitly described. As such, although the terms "step" and/or "block" can be used herein to connote different elements of system and/or methods, the terms should not be interpreted as implying any particular order and/or dependencies among or between various components and/or steps herein disclosed unless and except when the order of individual steps is explicitly described. The present disclosure will now be described more fully herein with reference to the accompanying drawings, which may not be drawn to scale and which are not to be construed as limiting. Indeed, the present invention can be embodied in many different forms and should not be construed as limited to the aspects set forth herein. Further, it will be apparent from this Detailed Description that the technological solutions disclosed herein are only a portion of those provided by the present invention. As such, the technological problems, solutions, advances, and improvements expressly referenced and explained herein should not be construed in a way that would limit the benefits, improvements, and/or practical application of the discussed aspects of the present invention.

The healthcare cloud computing platform of embodiments of the invention, advances interoperability between healthcare systems, public records, and electronic medical record vendors. The healthcare cloud computing platform allows for more accurate data to be added to an existing patient's electronic medical record by evaluating records from a third-party database using a state manager and normalization of records to a FHIR standard. The healthcare cloud computing platform removes duplicate records, does a side-by-side reconciliation of new records, and identifies trusted third-party database sources.

The healthcare cloud computing platform allows for automatic, without user intervention, seamless reconciliation of medical data for patients. The healthcare cloud computing platform is operable across various venues of care, including ambulatory, acute, emergency, and specialized care. The healthcare cloud computing platform is an immersive and efficient experience for clinicians to evaluate and view third-party patient health history, documents and results. It also reduces the need to review duplicate clinical data and removes unnecessary clinician interaction from trusted sources. Profile data is displayed in a side-by-side view that is more conducive and intuitive to cognitive comparison needed when evaluating subjective data. Graphical user interfaces of the healthcare cloud computing environment allow clinicians to view a third-party data that has been evaluated by the healthcare cloud computing environment along with data that is written to the patient's electronic medical record. The healthcare cloud computing platform of the present application provides providers and clinicians a more efficient experience with comprehensive patient records with a streamlined user experience.

Figure 1B:
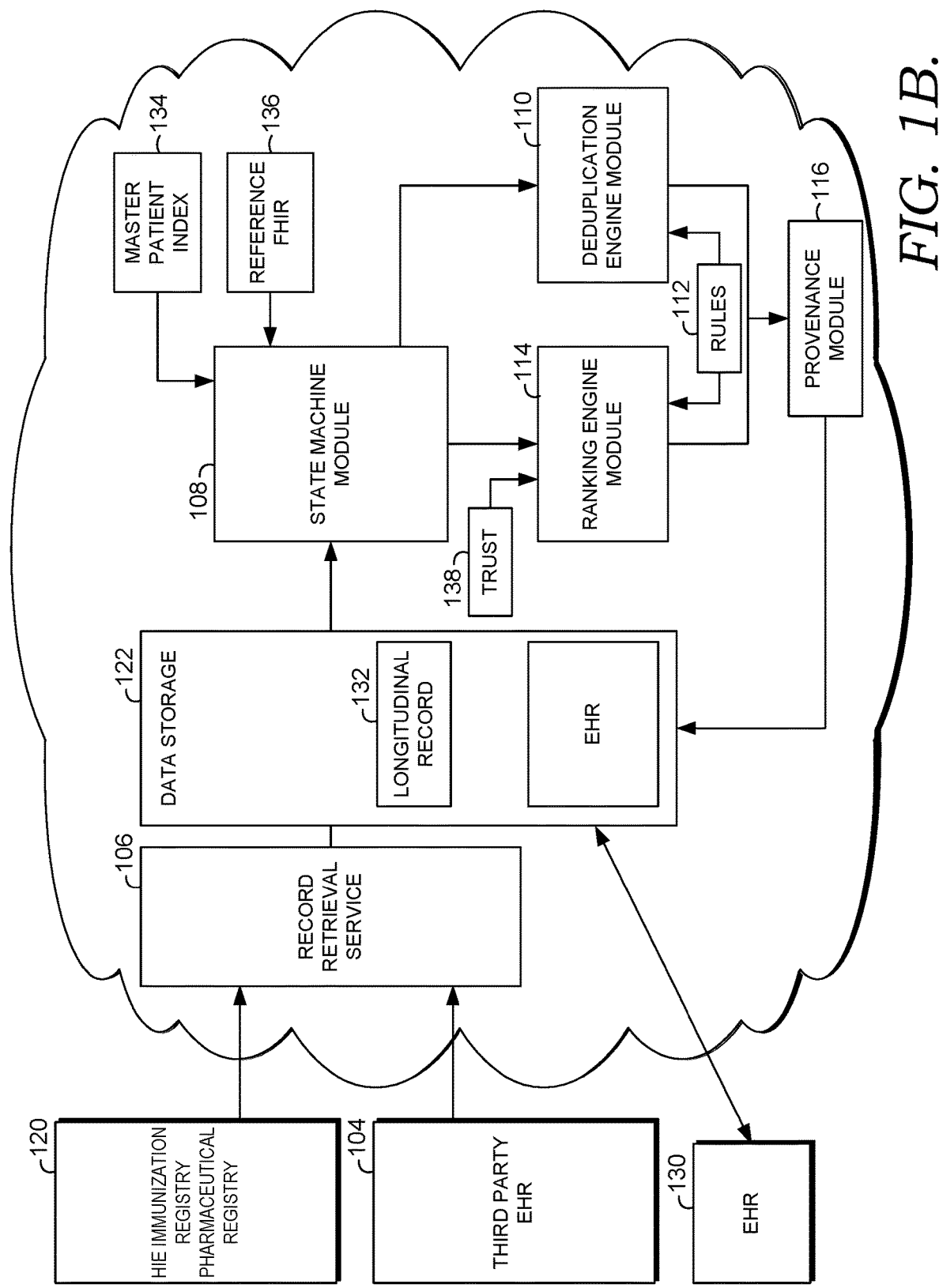

FIGS. 1A and 1B illustrate a system 100 configured to be useful in a computer healthcare system to consume clinical quality language queries in a programmatic manner, in accordance with one or more implementations. In some implementations, system 100 may include one or more healthcare cloud computing platforms 102. Computing platform(s) 102 may be configured to communicate with one or more remote platforms 104 according to a client/server architecture, a peer-to-peer architecture, and/or other architectures. Remote platform(s) 104 may be configured to communicate with other remote platforms via computing platform(s) 102 and/or according to a client/server architecture, a peer-to-peer architecture, and/or other architectures. Users may access system 100 via remote platform(s) 104.

In some implementations, computing platform(s) 102, remote platform(s) 104, and/or external resource(s) 120 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which computing platform(s) 102, remote platform(s) 104, and/or external resource(s) 120 may be operatively linked via some other communication media.

A given remote platform 104 may include one or more processors configured to execute computer program modules. The computer program modules may be configured to enable an expert or user associated with the given remote platform 104 to interface with system 100 and/or external resource(s) 120, and/or provide other functionality attributed herein to remote platform(s) 104. By way of non-limiting example, a given remote platform 104 and/or a given computing platform 102 may include one or more of a server, a desktop computer, a laptop computer, a handheld computer, a tablet computing platform, a NetBook, a Smartphone, a gaming console, and/or other computing platforms.

External resources 120 may include sources of information outside of system 100, external entities participating with system 100, and/or other resources.

Computing platform(s) 102 may include electronic storage 122, one or more processors 124, and/or other components. Computing platform(s) 102 may include communication lines, or ports to enable the exchange of information with a network and/or other computing platforms. Illustration of computing platform(s) 102 in FIG. 1A is not intended to be limiting. Computing platform(s) 102 may include a plurality of hardware, software, and/or firmware components operating together to provide the functionality attributed herein to computing platform(s) 102. For example, computing platform(s) 102 may be implemented by a cloud of computing platforms operating together as computing platform(s) 102.

Electronic storage 122 may comprise non-transitory storage media that electronically stores information. The electronic storage media of electronic storage 122 may include one or both of system storage that is provided integrally (i.e., substantially non-removable) with computing platform(s) 102 and/or removable storage that is removably connectable to computing platform(s) 102 via, for example, a port (e.g., a USB port, a firewire port, etc.) or a drive (e.g., a disk drive, etc.). Electronic storage 122 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 122 may include one or more virtual storage resources (e.g., cloud storage, a virtual private network, and/or other virtual storage resources). Electronic storage 122 may store software algorithms, information determined by processor(s) 124, information received from computing platform(s) 102, information received from remote platform(s) 104, and/or other information that enables computing platform(s) 102 to function as described herein.

Processor(s) 124 may be configured to provide information processing capabilities in computing platform(s) 102. As such, processor(s) 124 may include one or more of a digital processor, an analog processor, a digital circuit designed to process information, an analog circuit designed to process information, a state machine, and/or other mechanisms for electronically processing information. Although processor(s) 124 is shown in FIG. 1A as a single entity, this is for illustrative purposes only. In some implementations, processor(s) 124 may include a plurality of processing units. These processing units may be physically located within the same device, or processor(s) 124 may represent processing functionality of a plurality of devices operating in coordination. Processor(s) 124 may be configured to execute modules 106, 108, 110, 112, 114, and/or 116, and/or other modules. Processor(s) 124 may be configured to execute modules 106, 108, 110, 112, 114, and/or 116, and/or other modules by software; hardware; firmware; some combination of software, hardware, and/or firmware; and/or other mechanisms for configuring processing capabilities on processor(s) 124. As used herein, the term "module" may refer to any component or set of components that perform the functionality attributed to the module. This may include one or more physical processors during execution of processor readable instructions, the processor readable instructions, circuitry, hardware, storage media, or any other components.

It should be appreciated that although modules 106, 108, 110, 112, 114, and/or 116 are illustrated in FIG. 1A as being implemented within a single processing unit, in implementations in which processor(s) 124 includes multiple processing units, one or more of modules 106, 108, 110, 112, 114, and/or 116 may be implemented remotely from the other modules. The description of the functionality provided by the different modules 106, 108, 110, 112, 114, and/or 116 described below is for illustrative purposes, and is not intended to be limiting, as any of modules 106, 108, 110, 112, 114, and/or 116 may provide more or less functionality than is described. For example, one or more of modules 106, 108, 110, 112, 114, and/or 116 may be eliminated, and some or all of its functionality may be provided by other ones of modules 106, 108, 110, 112, 114, and/or 116. As another example, processor(s) 124 may be configured to execute one or more additional modules that may perform some or all of the functionality attributed below to one of modules 106, 108, 110, 112, 114, and/or 116.

Computing platform(s) 102 may be configured by machine-readable instructions 105. Machine-readable instructions 105 may include one or more instruction modules. The instruction modules may include computer program modules. The instruction modules may include one or more of record retrieval module 106, state machine module 108, deduplication module 110, rules module 112, ranking engine module 114, and provenance module 116, and/or other instruction modules.

Platform 102 may be Cerner HealtheIntent as shown in FIG. 1B. Platform 102 can ingest third-party clinical content/knowledge at scale to support an interoperable clinical knowledge management ecosystem. Platform 102 delivers knowledge-based products, such as quality measures, clinical pathways, and consumer engagement by integrating third-party intelligence into care delivery processes. Platform 102 comprises information from multiple EHR databases, such as multiple hospital systems.

Record retrieval module 106 is configured to read records from an external resource 120 or third party EMR 104. Record retrieval module 106 discovers and consolidates clinical medical data for an individual found across health networks and third party EMRs. Record retrieval module 106 initiates an interoperability process by triggering the record querying process to retrieve external resources 120. External resources 120 include third-parties, such as health information exchange (HIE), immunization registry, governmental healthcare registry, pharmaceutical registry, and third-party electronic medical record provider. Clinical medical data for individuals exists in a variety of different sources, such as National Exchange thru CommonWell and Carequality, state/regional HIEs, consumers, consumer devices, hospitals, ambulatory practices, pharmacy claims, and fill data from pharmacy databases, such as Surescripts, state vaccination registries, and other connected venues of care. Third party EMRs 104 are electronic medical records hosted by different vendors and separate from healthcare cloud computing platform 102. External resources 120 and third party EMRs 104 are collectively known as third-party databases for this application and are disparate computing systems and EMR vendors from the healthcare cloud computing platform 102.

The external resources 120 and third party EMRs 104 are maintained separate from the healthcare cloud computing platform. Registrations, admissions, transfers, and discharges from a healthcare facility can all be configured as triggers for record retrieval by module 106. For ambulatory and clinic-based locations, record retrieval module 106 may also be triggered by upcoming scheduled appointments. Additional triggers may be built in and process on a regular basis, like nightly or weekly batch processing.

Record retrieval module 106 plugs into an external resource's existing connection or exchange technology. In one embodiment, record retrieval module 106 utilizes application program interfaces to access external resources/third-party databases 120. The clinical data retrieved from external resources 120 is then sent to a healthcare cloud computing platform 120, including but not limited to Healthe Intent-Longitudinal Record. Record retrieval module 106 queries and retrieves clinical data automatically, without user intervention, so that a clinician or provider has access to the information before seeing a patient.

The clinical healthcare data from the external resources 120 received by the healthcare cloud computing platform 120 is aggregated. The healthcare cloud computing platform 120 also consumes direct data sources, such as a clinical electronic medical record system, such as Cerner Millennium.

Generally, EMRs 130 of FIG. 1B (sometimes referred to as electronic health records (EHRs)), may comprise data comprising electronic clinical documents, such as images, clinical notes, orders, summaries, reports, analyses, information received from clinical applications, and medical devices, or other types of electronic medical documentation relevant to a particular patient's condition and/or treatment. The patient data from EMR 130 may persist in a local copy of the patient's EMR or may be stored in a cloud computing environment such as healthcare cloud computing platform 102. Electronic clinical documents may contain various types of information relevant to the condition and/or treatment of a particular patient and can include information relating to, for example, patient identification information, images, alert history, previously consumed neuropsychiatric drugs, culture results, patient-entered information, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, clinician assignments, and a host of other relevant clinical information. Further, in some embodiments, patient data stored in the EMR may include patient demographic data, such as age, sex, race, nationality, socioeconomic status, marital status, and employment status and history. This data may further include the patient's insurance information, such as the insurance provider and the type of plan. Additional patient data may include previous and current home and work addresses.

Other types of patient data stored in the EMR may include current patient data and historical patient data. In exemplary aspects, current patient data includes data relating to the patient's labs, vitals, diagnoses, and medications from a current encounter (e.g., a current admission to a healthcare facility, a current visit to an outpatient facility, or a current period of receiving home healthcare services). The current patient data may include a diagnosis and/or treatment (including medications administered or ordered and procedures performed or ordered). During the current encounter, the patient may be diagnosed or treated with a condition, such as asthma, cancer, or heart disease, for example. Current patient data may further include lab results (e.g., physiological data), including vital sign data, from the current encounter. Historical patient data may include information about the patient's past encounters at the current healthcare facility or other healthcare facilities, past encounters at a post-acute care facility, etc. In some embodiments, historical patient data includes previous diagnoses, medications, and lab results.

Further, this patient data may be received from different sources thus constituting the patient's longitudinal record 132. In other embodiments, data relating to the patient's current condition and/or patient demographics may be received directly from a user, such as the patient or a care provider, inputting such information into a user device. Patient data for the longitudinal record 132 may come from the patient's EMR 130, data from third party EMRs 104 for the patient, external resources 120. Some current patient data, such as patient variable values, may be received from one or more sensors or monitoring devices or directly from a laboratory running the laboratory procedures. Additionally, historical patient information may be received from the patient's EMR and/or from insurance claims data for the patient. For example, data from in-home care services, hospitals, or any healthcare facility may be received. In an alternative embodiment, the patient's history may be received directly from the patient, such as during registration when admitted to a care facility for the current encounter or starting the current care services (such as with in-home care services).

Medical data elements may include patient condition, orders, patient demographic information (age, gender, height, weight), vital signs, test results, images, medications, medication administration, tasks, facility information, and caregiver information. The database record store 122 includes medical data elements from a variety of electronic health records, such medical data elements directly from the patient's EMR, such as Cerner Millennium, and utilizing the modules 106, 108, 110, 112, 114, and 116 data that has been transferred and consumed by the healthcare cloud computing resource 102 from external resources 120 and third party EHRs 104, such third-party databases (flat files, CCD and HL7) as shown in FIG. 1B.

The healthcare cloud computing platform, utilizing state machine module 108, deduplication module 110, rules module 112, ranking engine module 114, and provenance module 116, assembles the data collected from different sources into a single longitudinal record 132 for any given patient and is stored in electronic storage 122 of healthcare cloud computing platform 102. Once assembled into a longitudinal record 132, the aggregated data is available for analytics and for provider and clinician workflows using an EMR format, such as Cerner Millennium.

State machine module 108 processes medical data received from external resources 120. State machine module 108 reads the new data received from external source(s) 120 and normalizes the data utilizing FHIR standards. State machine module 108 uses state transformation to read and transform data from external resource(s) 120. State machine module 108 performs parallel reads and transformations such that information for multiple patients and/or from multiple resources can be performed efficiently.

State machine module 108 has state machine definitions and only after one definition is completed will the next occur. State machine definitions may be based on medical concept, where each medical concept has multiple medical properties defined to be evaluated. For example, a medical concept includes one or more of the healthcare organization, practitioner, encounters, problems, encounter diagnosis, allergies, medications, immunizations, procedures vials general lab results, CCD, clinical notes, pathology documents, cardiology documents, radiology documents, and microbiology documents.

The medical properties included for each medical concept may include patient name identifiers, comparison lists, values, systems, medical coding, text data, date of onset, date of documentation, condition type, and diagnosis coding. For example, for the medical concept Allergies, described below, the following medical properties would be read and transformed by state manager module 108.

```
class: org.hl7.fhir.r4.model.AllergyIntolerance
groups:
  - id: 0
    properties:
      - name: code.text
      - name: code.coding
        comparator: listOneMatch
        properties:
          - name: code
          - name: system
```

In one embodiment, the state machine definitions are object fields that are defined by JavaScript Object Notation (Json). This structure of state machine modules 108 allows for additional medical concepts with corresponding medical properties to be added to the state manager module 108. In one embodiment, state machine module performs simultaneous parallel reads and transformations of medical data for multiple patients from the third-party database are performed by the healthcare cloud computing platform 102. In another embodiment, state machine module 108 performs parallel reads and transformations of medical data for an individual patient from multiple third-party databases utilizing state transformation. For example, a parallel read and transformation of different medical records for an individual patient are performed simultaneously. Medical Records 1 and 3 are read from the external resources 120 and third party EHR 104 (HIE 1 and third party EMR 2) and converted using state manager module 108. The medical data from external resources 120 and third party EMR 2 is read for the Allergy concept, described above, and are converted from the multiple medical properties for the Allergy medical concept into Fast Healthcare Interoperability Resources (FHIR) under the HL7 standards. If needed, the medical records 2 and 4 from the primary record (130 or 132), EMR 1, such as Cerner Millennium or Longitudinal Record, for the patient, is read and normalized as well.

Medical Record 1:

```
"identifier": [
    {
        "system": ""system": "http://www.examplehie.com",
        "value": "1"
    }
],
"clinicalStatus": {
    "coding": [
        {
            "system": "http://terminology.hl7.org/CodeSystem/
                allergyintolerance-clinical",
            "code": "active",
            "display": "Active"
        }
    ]
},
"verificationStatus": {
    "coding": [
```

```
            {
                "system": "http://terminology.hl7.org/CodeSystem/
                    allergyintolerance-verification",
                "code": "confirmed",
                "display": "Confirmed"
            }
        ]
    },
    "type": "allergy",
    "category": [
        "food"
    ],
    "criticality": "medium",
    "code": {
        "coding": [
            {
                "system": "http://snomed.info/sct",
                "code": "714332003",
                "display": "Banana allergy"
            }
        ],
        "text": "Banana allergy"
    },
    "patient": {
        "reference": "Patient/23456342"
    },
    "onsetDateTime": "2004",
    "recordedDate": "2014-10-09T14:58:00+11:00",
    "recorder": {
        "reference": "Practitioner/235345"
    },
    "asserter": {
        "reference": "Patient/23456342"
    },
    "lastOccurrence": "2012-06",
    "note": [
        {
```

Medical Record 2:

```
"identifier": [
    {
        "system": "Cerner",
        "value": "2"
    }
],
"clinicalStatus": {
    "coding": [
        {
            "system": "http://terminology.hl7.org/CodeSystem/
                allergyintolerance-clinical",
            "code": "active",
            "display": "Active"
        }
    ]
},
"verificationStatus": {
    "coding": [
        {
            "system": "http://terminology.hl7.org/CodeSystem/
                allergyintolerance-verification",
            "code": "confirmed",
            "display": "Confirmed"
        }
    ]
},
"type": "allergy",
"category": [
    "food"
],
"criticality": "medium",
"code": {
    "coding": [
        {
            "system": "http://snomed.info/sct",
            "code": "714332003",
            "display": "Banana allergy"
        }
    ],
    "text": "Green Banana allergy"
```

```
    },
    "patient": {
        "reference": "Patient/23456342"
    },
    "onsetDateTime": "2004",
    "recordedDate": "2014-10-09T14:58:00+11:00",
    "recorder": {
        "reference": "Practitioner/235345"
    },
    "asserter": {
        "reference": "Patient/23456342"
    },
    "lastOccurrence": "2012-06",
    "note": [
        {
```

Medical Record 3

```
    },
    "identifier": [
        {
            "system": "http://acme.com/ids/patients/risks",
            "value": "49476534"
        }
    ],
    "clinicalStatus": {
        "coding": [
            {
                "system": "http://terminology.hl7.org/CodeSystem/
                    allergyintolerance-clinical",
                "code": "active",
                "display": "Active"
            }
        ]
    },
    "verificationStatus": {
        "coding": [
            {
                "system": "http://terminology.hl7.org/CodeSystem/
                    allergyintolerance-verification",
                "code": "confirmed",
                "display": "Confirmed"
            }
        ]
    },
    "type": "allergy",
    "category": [
        "food"
    ],
    "criticality": "high",
    "code": {
        "coding": [
            {
                "system": "http://snomed.info/sct",
                "code": "213021008",
                "display": "Peanut allergy"
            }
        ],
        "text": "Peanut allergy"
    },
    "patient": {
        "reference": "Patient/23456342"
    },
    "onsetDateTime": "2004",
    "recordedDate": "2014-10-09T14:58:00+11:00",
    "recorder": {
        "reference": "Practitioner/23566"
    },
    "asserter": {
        "reference": "Patient/23456342"
    },
    "lastOccurrence": "2012-06",
    "note": [
        {
            "text": "The criticality is high becasue of the observed
                anaphylactic reaction when challenged with cashew extract."
        }
    ],
    "reaction": [
        {
```

```
    "substance": {
      "coding": [
        {
          "system": "http://www.nlm.nih.gov/
            research/umls/rxnorm",
          "code": "1160593",
          "display": "Peanut allergenic extract Injectable Product"
        }
      ]
    },
    "manifestation": [
      {
        "coding": [
          {
            "system": "http://snomed.info/sct",
            "code": "39579001",
            "display": "Anaphylactic reaction"
          }
        ]
      }
    ],
    "description": "Challenge Protocol. Severe reaction to
subcutaneous cashew extract. Epinephrine administered",
    "onset": "2012-06-12",
    "severity": "severe",
    "exposureRoute": {
      "coding": [
        {
          "system": "http://snomed.info/sct",
          "code": "34206005",
          "display": "Subcutaneous route"
        }
      ]
    }
  },
  {
    "manifestation": [
      {
        "coding": [
          {
            "system": "http://snomed.info/sct",
            "code": "64305001",
            "display": "Urticaria"
          }
        ]
      }
    ]
```

Medical Record 4:

```
"identifier": [
  {
    "system": "Cerner",
    "value": "2"
  }
],
"clinicalStatus": {
  "coding": [
    {
      "system": "http://terminology.hl7.org/CodeSystem/
        allergyintolerance-clinical",
      "code": "active",
      "display": "Active"
    }
  ]
},
"verificationStatus": {
  "coding": [
    {
      "system": "http://terminology.hl7.org/CodeSystem/
        allergyintolerance-verification",
      "code": "confirmed",
      "display": "Confirmed"
    }
  ]
},
"type": "allergy",
"category": [
  "food"
],
"criticality": "high",
```

```
"code": {
  "coding": [
    {
      "system": "http://snomed.info/sct",
      "code": "213021008",
      "display": "Peanut allergy"
    }
  ],
  "text": "Peanut allergy"
},
"patient": {
  "reference": "Patient/23456342"
},
"onsetDateTime": "2004",
"recordedDate": "2014-10-09T14:58:00+11:00",
"recorder": {
  "reference": "Practitioner/23566"
},
"asserter": {
  "reference": "Patient/23456342"
},
"lastOccurrence": "2012-06",
"note": [
  {
```

Figure 8:
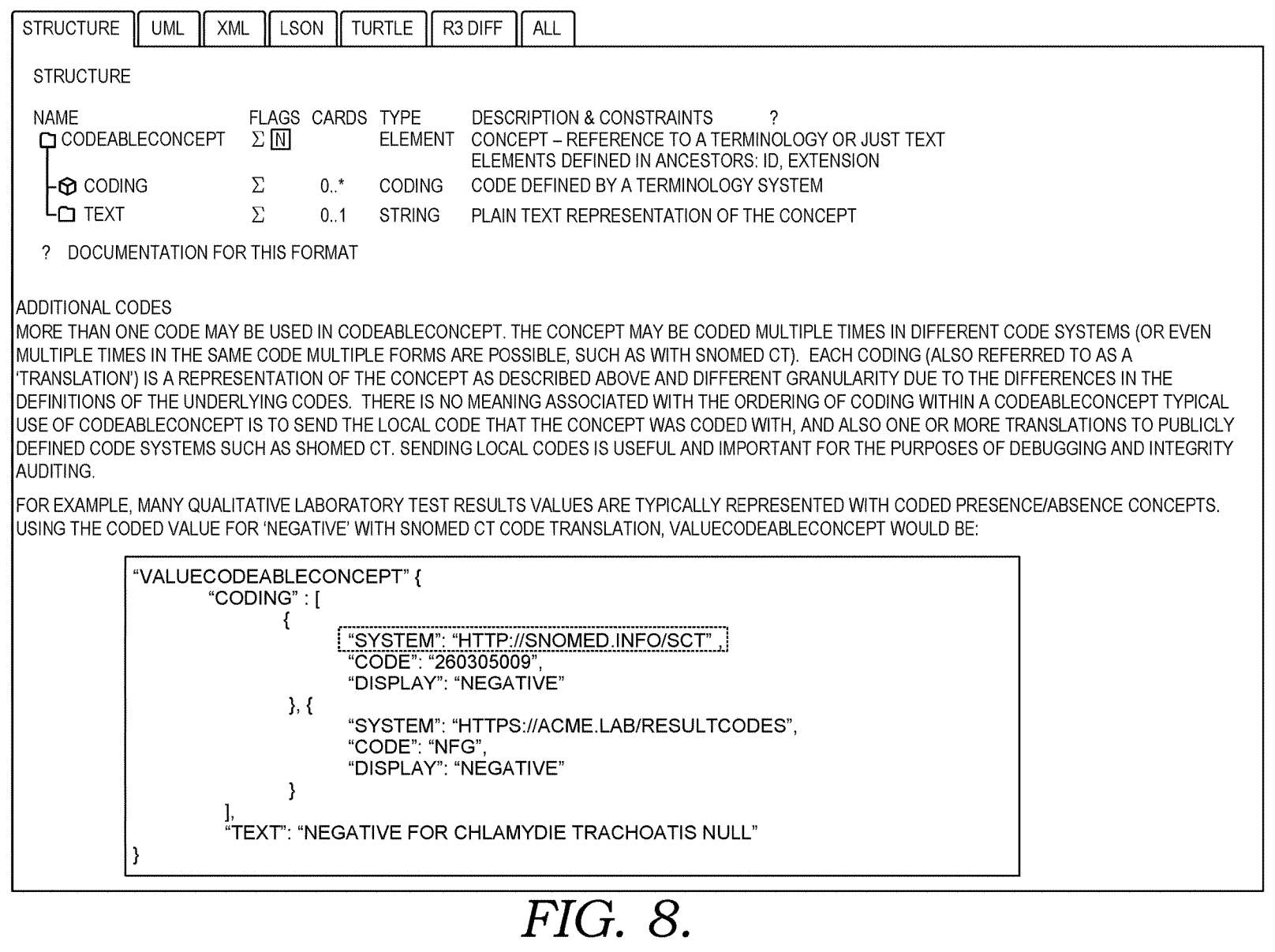

Exemplary reference database 136 of FIG. 1B for Fast Healthcare Interoperability Resources (FHIR) under the HL7 standards shown in FIG. 8. FIG. 9 is an exemplary medical concept using FHIR standards and the multiple medical properties for the exemplary medical concept using the FHIR standards and structure. The exemplary medical concept with multiple FHIR medical properties may be applied to multiple different medical concepts further described in this specification. This allows for medical concepts and the multiple FHIR medical properties for the medical concepts to be elastic and flexible based on user preference and as additional information becomes known or desired about a particular medical concept. In one embodiment, the medical concepts and multiple FHIR medical properties for the concept are built using YAML Ain't Markup Language (YAML) and Spring Expression Language (SPEL). YAML is a human-readable data-serialization language used for configuration files and in applications where data is being stored or transmitted. SPEL is powerful expression language that supports querying and manipulating an object graph at runtime. SPEL syntax provides method invocation and basic string templating functionality. YAML and SPEL give context to the medical concepts and medical properties and rules. This allows for a medical concept and rule developer, who may be less experienced in computer programming, to build the medical concepts, medical properties and rules using libraries of code compare medical properties normalized to FHIR without having to write brand new code allowing for many medical concepts, medical properties and rules to be built and executing using healthcare cloud computing platform 102. A developer can access a FHIR type utilizing YAML and define rules without writing code and use SPEL expressions to compare the FHIR types without writing additional code.

After a developer has defined the medical concepts, medical properties and rules, when triggered, medical records 1 and 3 (and 2 and 4, if needed) for the patient are read and converted accordingly to FHIR medical properties for the allergy medical concept. The medical properties for the exemplary allergy medical concept include provider identifier, clinical status, verification status, type, criticality, text, patient, onset date, patient reference, and last occurrence. Each of these medical properties include multiple subproperties according to FHIR standards. For example, medical property type "allergy" includes a subproperty for "category". In this instance, the subproperty for type "allergy" is "food". Medical data from external resources 120 and third party EMRs 104 is read and transformed by state machine module 108 for a medical concept and its properties and subproperties providing an accurate and systemic way to read and normalize medical data from multiple resources and allows the normalized medical data to be compared and interrogated as described in more detail with respect to embodiments of the invention.

Referring again to FIG. 1A, the medical concepts and associate medical properties read and normalized by the state machine module 108 is stored in provenance module 116 as being normalized and read. This provides historically documentations of what third-party databases (and patient documents) have been read and normalized by state machine module 108. Data provenance captures source/history information.

When the record retrieval module 106 is triggered, it pulls the patient's record (130 or 132) from electronic storage 122 and reads and normalized data from external resources 120 that has been processed by state machine module 108.

Deduplication module 110 compares read and normalized data for the patient from the one or more external resource(s) 120 to data from the patient's record (130 or 132) to identify new data not found in the patient's primary record (130 or 132). In one embodiment, initially the read and normalized data for the patient from one or more external resource(s) 120 is compared to data in the patient's EHR from an EHR system, such as Cerner Millennium, to create a longitudinal record 132 for a patient that has data from a primary EHR system 130, third party EHRs 104 and other external resources 120. Once a longitudinal record 132 exists or is created by the healthcare cloud computing platform 102, new data from one or more external resource(s) 120 is compared to the data for the patient in the patient's longitudinal record 132. This allows for a central repository of all data for a patient across multiple EHR systems 104, 130 and external resource(s) 120.

The deduplication module 110 accesses rules to determine whether data for a patient from an external resource 120 is duplicative of data already in the patient's record (130 or 132) module 110 receives the data from external resource 120 that has been read and normalized by state machine module 108. Deduplication module 110 accesses the patient's primary record (130 or 132). In some instances, the data in patient's EMR record 122 or longitudinal record 132 has been normalized according to FHIR standards.

Deduplication module 110 applies the rules from rules module 112 and compares the external resource 120 data for the patient to the data in the patient's record (130 or 132) to determine if the data from the external resource 120 is duplicative of that which is already in the patient's record (130 or 132). In one embodiment, for a medical concept, each of the medical properties for the medical concept are compared to determine if they are duplicates. For example, the deduplication module 110 compares the medical properties for the medical concept "allergy" for each of Medical Record 1 and Medical Record 2. In this example, Medical Record 1 (HIE 1) is a record for the patient from an external resource 120 regional HIE and Medical Record 2 (EMR 1) is the primary record for the patient (130 or 132).

With reference to FIG. 3, for the medical concept "allergy" the deduplication module 110 applies rules from rules module 112 to determine whether an allergy from an external record 120 is duplicative of an allergy in the patient's record (130 or 132) by comparing the medical properties "patient", "coding", "text", and "date of "onset" from the external record 120 and patient's EMR to determine if they match when normalized to FHIR standards. As can be seen, the medical properties of "patient", "coding", and "date of onset" match but the "text" property does not match between Medical Record 1 (HIE 1) and Medical Record 2 (EMR 1). Thus, based on the rule set 112 for the allergy concept, the deduplication module 110 would determine that Medical Record 1 (HIE) is not duplicative of allergies already in the patient's primary record (130 or 132) because all medical properties do not match.

Thus, provenance module 116 will store that the HIE 1 and EMR 1 have been read, normalized and compared with one another to determine if they are duplicative. With reference to FIG. 1B, since the deduplication module 110 has determined that the allergy in HIE 1 is not duplicative data in patient's primary record EMR 1, the allergy from HIE 1 is written into the patient's longitudinal record 132. As such, both the allergies from both HIE 1 and EMR 1 will persist in the patient's long term medical record 132.

The deduplication module 110 determines that the clinical data for the patient from external resource HIE 1 (120) is new and not duplicative what is already in the patient's record 132, and will be displayed to a clinician in within the standard workflow of the EMR/Longitudinal record 132 as being part of the patient's record. In one embodiment, the clinical data added to the patient's longitudinal record 132 from an external resource is flagged and identified as "new" to a clinician if it is new to the system and/or the clinician has not seen the new data from the external resource previously.

In another embodiment, the clinical data from an external resource 120 that has been identified as new for the patient's longitudinal record 132 will be posted to a clinician and identified as new. The clinician will can review the clinical data from the external resource 120 and select to post or write the data to the patient's longitudinal record 132.

With continued reference to FIG. 3, in another example, the medical properties of "patient", "coding", "text", and "date of onset" match between Medical Record 3 (HIE 2) and Medical Record 4 (EMR 1). Thus, based on the rule set 112 for the allergy concept, the deduplication module 110 would determine that HIE 2 is duplicative of an allergy already in the patient's primary record (EMR 1) because all medical properties match.

Thus, provenance module 116 will store for HIE 2 and EMR 1 that medical concept and its properties have been read, normalized and compared with one another to determine if they are duplicative. The provenance module 116 will store that the HIE 2 peanut allergy is related to the patient's primary record (EMR 1) peanut allergy and provide a link or pointer to HIE 2 data. The provenance module stores historical data regarding what external records 120, EHR records 130 and third party EHR records have been read, normalized and compared and the outcome of the comparison for a given medical concept. However, the patient's longitudinal record 132 is the official record for the patient.

With Reference to FIG. 1B, since the deduplication module 110 has determined that the allergy in third party EMR 2 is duplicative of data in patient's primary record EMR 1, the allergy from patient's primary record EMR 1 is maintained for the patient and the allergy from third party EMR 2 is not written into the patient's longitudinal record 132. The allergy from the patient's primary record EMR 1 will persist in the patient's long term medical record 132. The allergy from the EMR 2 will be stored in the provenance module 116 and will be accessible to the clinician if the clinician chooses to review external records 120 and third party EMR records 104 reviewed by the deduplication module 110. In one embodiment, the clinician user, while view the patient's primary record (130 or 132) can drill down on the allergy of EMR 1 to see if there are an related external records 120 or third party EMR records 104 stored by the provenance module 110. However, the allergy from the EMR 1 will be the primary allergy for the patient in the patient's longitudinal record 132.

As described above, rules module 112 contains rules for applying to deduplication as well as ranking rules. While rules for deduplication determine whether an external resource 120 is duplicative of data already in the patient's primary record (130 or 132), ranking rules are applied when comparing clinical data for a patient that has been obtained from two outside resources such as external resources 120 and third party EHRs 104.

Ranking engine module 114 accesses the data read and normalized for two resources from outside the patient's primary record (130 or 132) for the patient. Accessing ranking rules 112 and trust repository 138, the ranking engine module 114, compares medical properties for a medical concept from the two outside resources. For example, with reference to FIG. 6, ranking engine module 114 is depicted to determine whether to write and store Allergy 1 from a first outside resource or Allergy 2 from a second outside resource to the patient's primary record (132). For example, Allergy 1 and Allergy 2 have been determined to be the same using the logic of deduplication module 110, and now they are ranked using rules from rules engine module 114. Rules engine module 114 has ranking rules and weights to apply to medical properties based on the medical concept. For example for the allergy medical concept of FIGS. 6 and 7, the ranking rules look to the medical properties of onset date and time (Rule 1), clinical status (Rule 2) and verification status (Rule 3) to determine which of the allergies to write to the patient's primary record (132). Each of rules 1, 2 and 3 has equal weighting of 0.33 for medical concept allergy. The occurrence (or number of occurrences) of the medical property in the outside resource is multiplied by the weighting factor. For example, the oldest onset allergy wins Rule 1. Rule 2 provides weighted criteria based on four clinical statuses (resolved, inactive, active and null). Rule 3 provides weighted criteria based on five possible verification statuses (entered in error, refuted, confirmed, unconfirmed and null). The outcomes of each of the rules is summed and the highest value is the winner. Thus, for comparing allergy 1 and allergy 2, allergy 1 is the winner with 0.66 sum and is written to the patient's primary record (132). The comparison and related data is for both allergy 1 and allergy 2 is written to provenance module 116 for later viewing if requested.

Similar to deduplication module 110, ranking engine module may either stage the winning outside resource record data for clinician review and verification before being entered into the patient's primary record (132). Staged data will require a provider or clinician to review and subsequently add the data to the patient's primary record (132). In another embodiment, the winning outside resource data may be directly written into the patient's primary record (132) which in some instances is the legal record.

Outside resource clinical data may be written into the record if it is determined to be from a trusted source 138. Healthcare organizations using the healthcare cloud computing platform 102 can identify outside sources (120 or 104) of patient data are deemed reliable and opt to directly write data from these outside sources (120 or 104). In addition, healthcare organizations can adjust trusted sources per medical concept. Directly written clinical data will automatically be written to the patient's primary legal record (132) without a clinical user's interaction.

Figure 2:
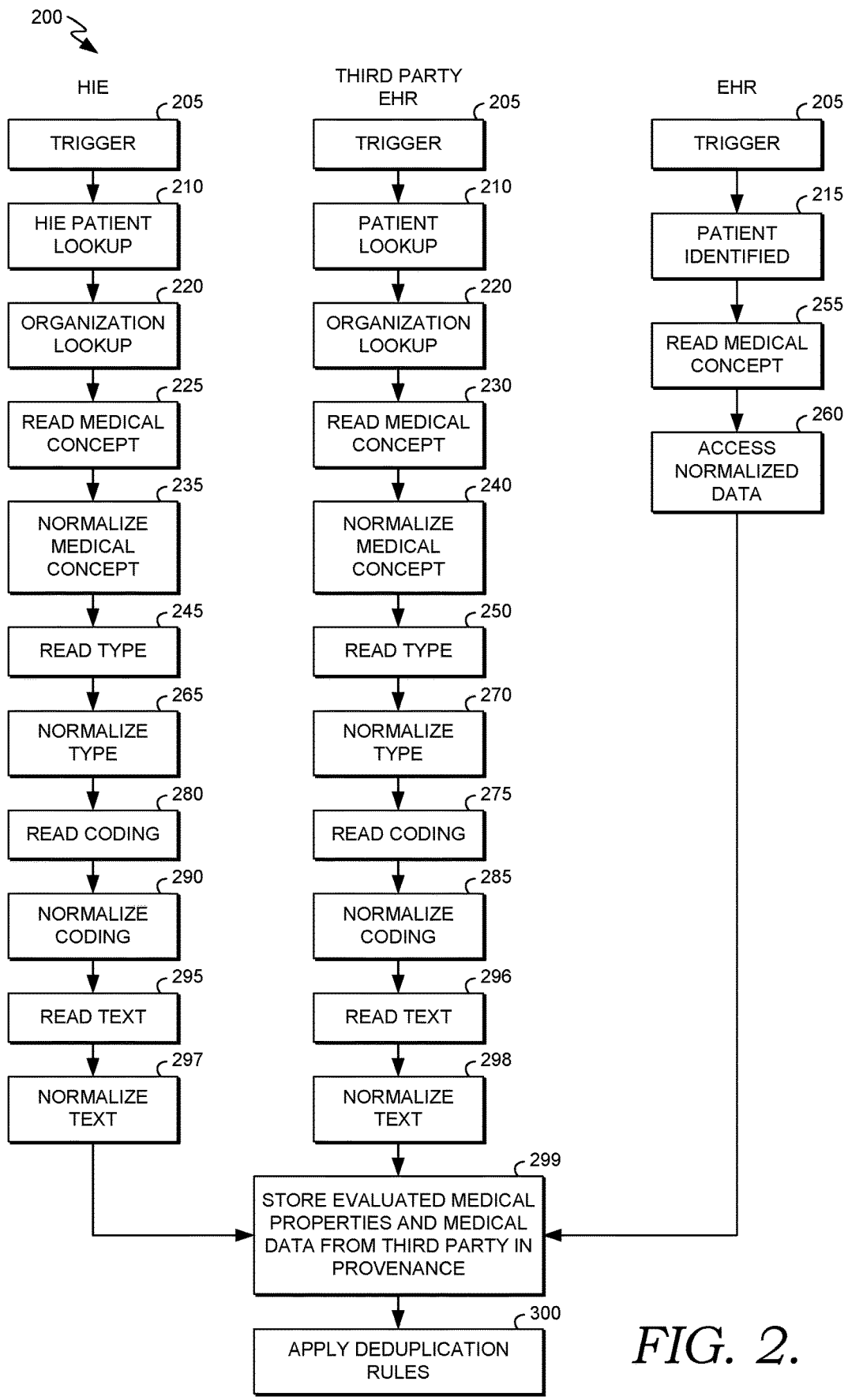
FIG. 2 depicts a flow chart of parallel reads of third-party databases, in accordance with embodiments of the invention.
Figure 4:
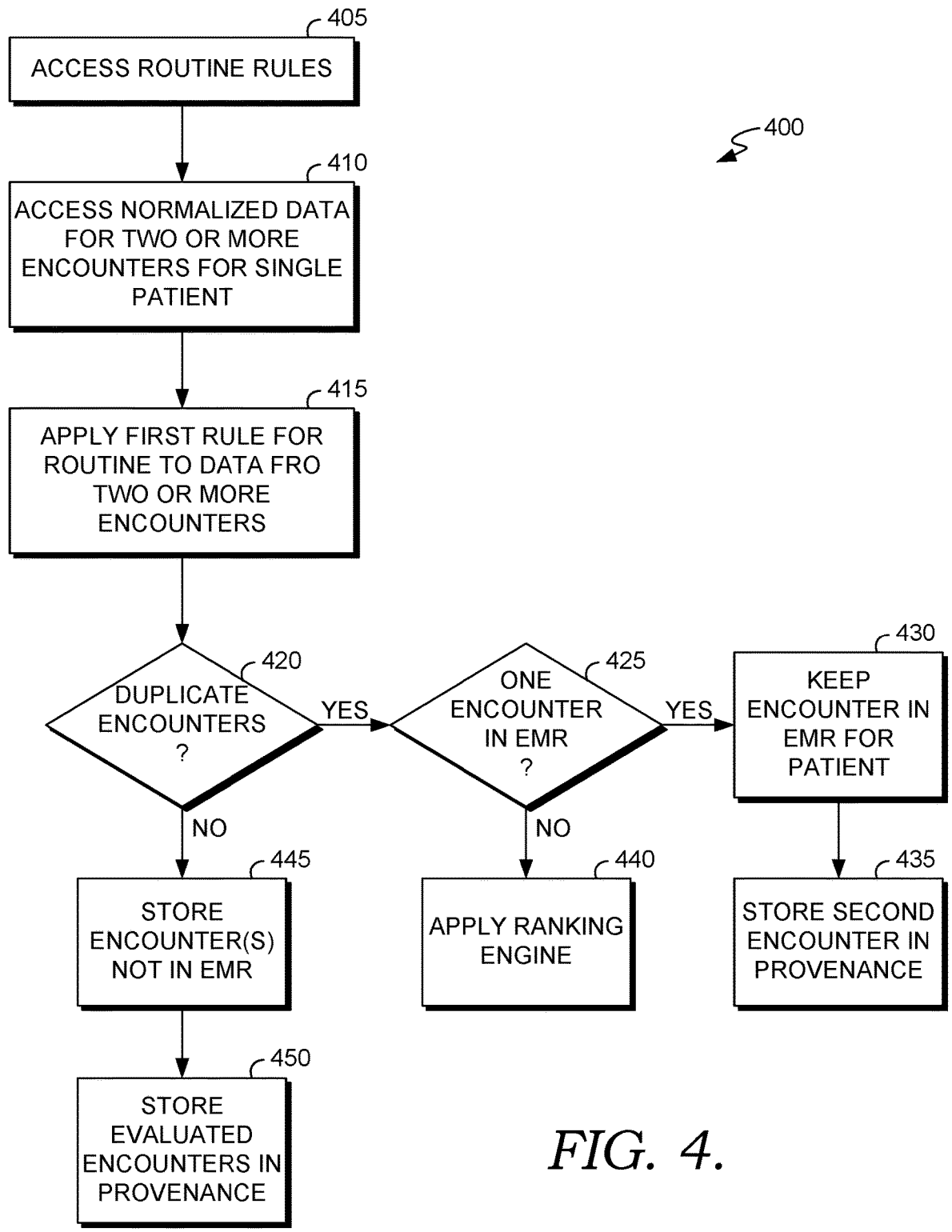
FIG. 4 depicts a flowchart of deduplication in accordance with aspects of the disclosure.
Figure 5:
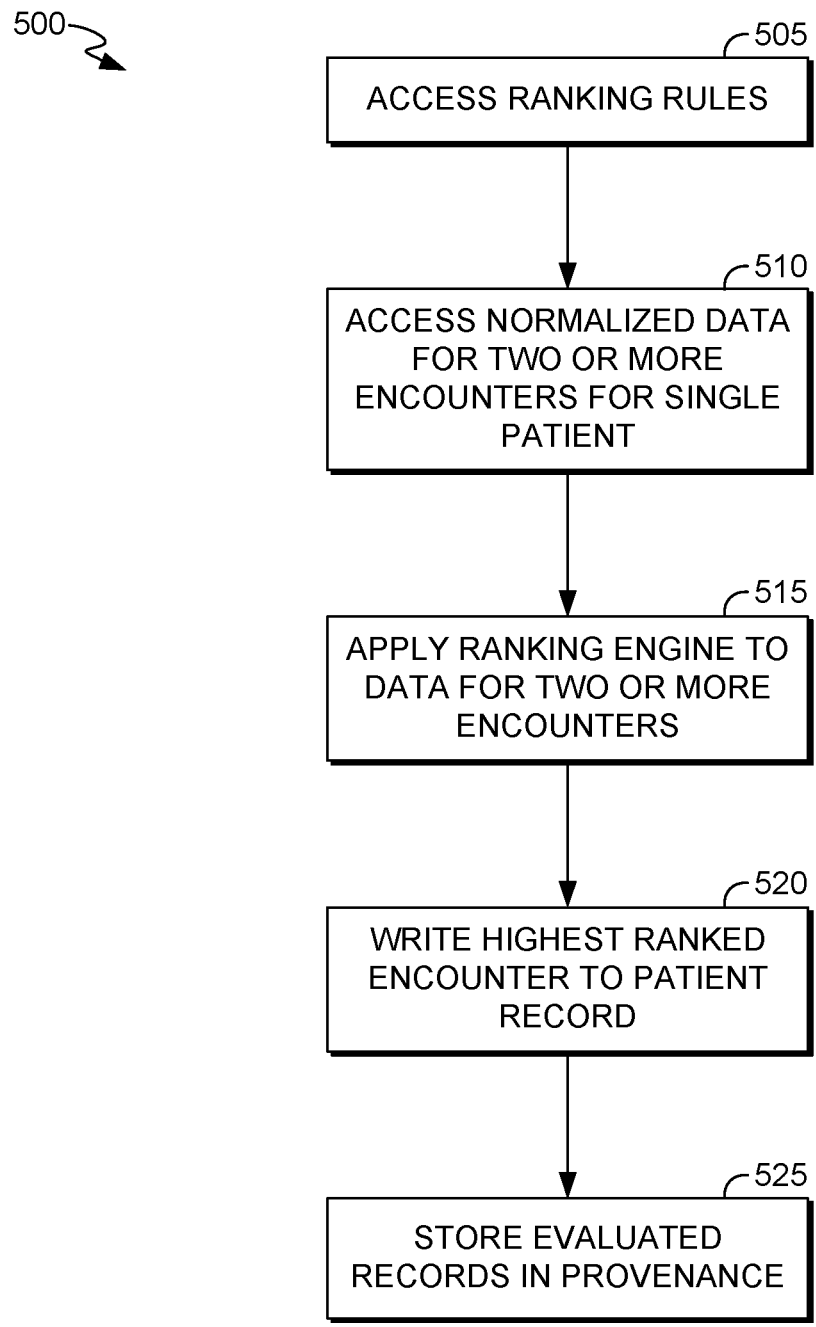
FIG. 5 depicts a flowchart of ranking in accordance with aspects of the disclosure.

FIGS. 2, 4 and 5 illustrates a methods useful in a healthcare cloud computing platform 102, in accordance with one or more implementations. With reference to FIG. 2, operations of method 200 presented below are intended to be illustrative. In some implementations, method 200 may be accomplished with one or more additional operations not described, and/or without one or more of the operations discussed. Additionally, the order in which the operations of method 200 are illustrated in FIG. 2 and described below is not necessarily limiting.

In some implementations, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

FIG. 2 illustrates method 200, in accordance with one or more implementations. An operation 205 may include receiving a trigger to begin method of claim 200. Method 200 may be performed by one or more hardware processors configured by machine-readable instructions including a module that is the same as or similar to state machine module 108, in accordance with one or more implementations.

An operation 210 may include looking up and identifying a patient to perform method 200. Operation 210 may read and normalize a patient identification from one or more outside patient records. For example, utilizing the example above with respect to Medical Records 1 and 3, patient information may be read, normalized and then compared to the master patient index 134 of FIG. 1B at operation 215. For example, "patient": {"reference": "Patient/23456342"} from Medical Records 1 and 3, may be determined to be patient "Jane Doe" in the patient's primary medical record (EMR 1) (130 or 132) from healthcare cloud computing platform 102.

An operation 220 may include looking up and identifying the organization for each record being analyzed. Operation 220 may read and normalize an organization from one or more outside patient records (HIE and third party HER). For example, utilizing the example above with respect to Medical Records 1 and 3, organization information may be read, normalized and then compared to trust 138 of FIG. 1B. For example, from Medical Record 1 the organization is determined to be {"system": ""system": "http://www.example-hie.com", "value": "49476534". Healthcare cloud computing platform 102 compares this information to trust 138 and determines Medical Record 1 comes from trusted HIE 1. From Medical Record 3, the organization is determined to be "identifier": [{"system": "http://acme.com/ids/patients/risks", "value": "49476534"}] and compares this information to trust 138. It is determined that Medical Record 3 comes from an untrusted third party EHR.

Operation 255 reads the medical concept that is going read, normalized and evaluated by state machine module 108. After reading the medical concept, the medical properties and clinical data from the patient's primary medical record (130 or 132) is accessed at operation 260. If needed, the data from the patient's primary medical record (130 or 132) is read and normalized by state machine module 108 as described below for trusted HIE 1 and untrusted third party EHR.

State machine module 108 initiates multiple operations to begin reading and normalizing data from multiple medical records according to the rules defined in rules engine module 112 for a medical concept. State machine module 108 creates multiple queues and states to be processed for multiple medical records and medical concepts. The multiple states include record retrieval, record normalization, patient lookup, organization lookup, and state completion. The state machine 108 has defined state machine definitions (Json). States are completed in order. For example, the first state must be completed before moving to a second state. The states are completed in parallel by state workers. This provides the piping or backbone to process business logic (rules) for multiple records and multiple medical records in parallel in a timely and efficient manner. The state machine module 108 and rules module 112 are maintained separately such that additional medical concepts, medical properties and business logic and rules may be added or deleted from rules module 112 without impacting the processing performed by state machine module 108.

Operations 225 and 230 identify the medical concept and defined medical properties to be read for. The identification of the medical concept to be read for may be provided by the healthcare cloud computing platform 102. For example, the healthcare cloud computing platform 102 may have standing instructions to read all medical records for the medical concept "allergies". Alternatively, based on the type of external resource 120 or third party EMR 104, the medical cloud computing platform 102 may be instructed to read for only particular medical concepts. For example, the healthcare cloud computing platform may be instructed to only read an immunization registry external resource 120 for the allergy medical concept.

Operations 235 and 240 normalize the medical concept, in this example, allergies. Operations 245 and 250 read the medical property "type" for the medical concept and operations 265 and 270 normalize "type". Operations 275 and 280 read the medical property "coding" for the medical concept and operations 290 and 285 normalize "coding". Operations 295 and 296 read the medical property "text" and operations 297 and 298 normalize "text". In these examples, the medical concepts and medical properties normalized in a FHIR standard as shown in Medical records 1 and 3 above.

Operation 260 accesses the normalized medical data for the medical concept and defined medical properties from the patient's primary record (130 or 132) to be compared with the data from outside resources read and normalized by state machine module 108.

Operation 299 stores data (or links) for external records 120 and third party EHRs 104 in a module that is the same or similar to provenance module 116. Operation 299 further stores that outside records have been read and normalize so that in the future the state machine module 108 knows that an outside record has been processed by the state machine module 108 to avoid having to read and normalize the data again. Operation 299 further stores that the outside record 120 or 104 has been read and normalized for an identified patient and organization and an identification that the outside record it is related to a medical concept or property in the patient's primary record (130 or 132). For example, operation 299 would store that Record 3 from EMR 2 was read and normalized and related to medical concepts and medical elements of Record 4 of the patient's primary medical record (EMR 1) (130 or 132).

FIG. 4 illustrates method 400, in accordance with one or more implementations. An operation 405 accesses duplication rules for method 400. Method 400 may be performed by one or more hardware processors configured by machine-readable instructions including a module that is the same as or similar to deduplication module 110 and accessing rules from a module that is the same as or similar to rules module 112, in accordance with one or more implementations. Operation 410 accesses the medical properties for a medical concept that have been read and normalized by state machine module 108. The rules to determine whether or not a medical record is duplicative or contains duplicate data to another medical record for a patient are stored in rules module 112.

Exemplary rules typically include conditional statements, conditional expressions and conditional constructs are features of a programming language. Different computations or actions are performed depending on whether a programmer-specified boolean condition evaluates to true or false. Rules may be achieved by selectively altering the control flow based on some condition.

As described above when discussing the healthcare cloud computing platform, a developer may define particular conditional expressions and constructs for a particular medical concept. For example, the rule set for a medical concept may compare identifiers between normalized data from two different medical records for a patient. It will be appreciated that the identifiers may be a single value, nested values or a list of values. An exemplary conditional rule to determine if a medical record is duplicative or contains duplicate data to another medical record for a patient is shown in FIG. 3.

Operator 420 determines if the medical properties for two different records indicate they are the same as another record. When operator 420 determines that the medical properties of a first record and a second record satisfy the conditional rule set, the data in the first and second record is deemed to be the same. If operator 425 determines that the medical property as the patient's primary record (130 or 132), operator 430 keeps the data in the patient's primary record (130 or 132) and operator 435 stores the outside record information and review in provenance module 116.

When operator 420 determines that the medical properties of a first record and a second record satisfies the conditional rule set, the data in the first and second record is deemed to be the same. Operator 425 determines that neither the first nor the second record are not the primary medical record (130 or 135) for the patient and thus operator 440 will apply the logic rules for ranking the records using ranking engine module 114.

Operator 420 determines if the medical properties for two different records indicate they are indeed different and not duplicative. When operator 420 determines that the medical properties of a first record and a second record do not satisfy the conditional rule set, the data in the first and second record is deemed to be different. Operator 445 writes medical record data not in the patient's primary record (132). In one embodiment, data from the two different records may not be in the patient's primary record and the data is stored in the patient's primary medical record (132). Additionally, operator 450 stores the evaluation of each record in provenance module 116.

FIG. 5 illustrates method 500, in accordance with one or more implementations. An operation 505 accesses ranking rules for method 500. Method 500 may be performed by one or more hardware processors configured by machine-readable instructions including a module that is the same as or similar to ranking engine module 114 and accessing rules from a module that is the same as or similar to rules module 112, in accordance with one or more implementations. Operator 510 accesses the medical properties for a medical concept that have been read and normalized by state machine module 108. The rules to determine to rank two outside medical records that have been deemed to be the same by deduplication module 110 for a patient are stored in rules module 112.

Exemplary rules typically include conditional statements, conditional expressions and conditional constructs are features of a programming language. In one embodiment, weights are assigned to different medical properties to rank the records as being more complete or accurate. Examplary ranking rules for the ranking engine module 114 are shown in FIGS. 6 and 7. Operator 515 applies the ranking rules for the identified medical concept and operator 520 write the medical data for the patient that ranks the highest is written into the patient's primary record (130 or 132). The lower ranking record and its evaluation is or links are stored by operator 525 in provenance module 116.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

The invention claimed is:

1. A method for documenting transformations of medical data maintained by a healthcare cloud computing platform, the method comprising:
    loading medical data from a third-party database into a healthcare cloud computing platform, the medical data comprising a first medical record and a second medical record;
    identifying a medical concept included in the medical data, wherein the medical concept includes a first plurality of medical properties in the first medical record and a second plurality of medical properties in the second medical record;
    transforming the medical data using a state machine having a state machine definition for the medical concept, to result in transformed medical data, by:
        providing the medical data to the state machine;
        determining a normalized plurality of medical properties for the medical concept according to the state machine definition; and
        normalizing the first plurality of medical properties and the second plurality of medical properties according to the state machine definition to generate a first normalized plurality of medical properties for the first medical record and a second normalized plurality of medical properties for the second medical record;
    mapping the transformed medical data to a primary medical record in the healthcare cloud computing platform based on the transformed medical data and the primary medical record being associated with a same patient identifier;
    evaluating the first medical record and the second medical record by accessing deduplication rules for the cloud computing platform to determine if the first medical record and the second medical record satisfy a rule set for the medical concept;
    if the first medical record and the second medical record satisfy the rule set:
        determining whether one of the first medical record and the second medical record is in the primary record;
        if the first medical record is in the primary record and the second medical record is not in the primary record: storing the second medical record in a provenance module;
        if the first medical record and the second medical record are not in the primary record:
            ranking the first medical record and the second medical record to determine a higher-ranking medical record and a lower-ranking medical record;
            writing the higher-ranking medical record into the primary medical record; and
            writing the lower-ranking medical record into the provenance module;
    if the first medical record and the second medical record do not satisfy the rule set:
        writing data from the first medical record and the second medical record that is not stored in the primary medical record into the primary medical record; and
        storing the determination that the first medical record and the second medical record do not satisfy the rule set in the provenance module.

2. The method of claim 1, comprising:
reconciling a first read of medical data with a second read of medical data according to a state machine definition; and
transforming a property of the primary medical record according to the reconciliation of the first read of medical data with the second read of medical data.

3. The method of claim 1, wherein
a first read of medical data from a first, third party database is reconciled with a second read of medical data from a second, third party database utilizing state transformation rules for a standardization of the medical data, and wherein the transformation of a property of the primary medical record is determined according to the state transformation rules.

4. The method of claim 1, wherein
a plurality of reads of medical data are performed from a plurality of third-party databases by the healthcare cloud computing platform.

5. The method of claim 4, wherein:
the plurality of reads of medical data are ranked according to a time rule, a clinical status rule, and a verification status rule; and the method comprises transforming a property of the primary medical record based a result of the ranking.

6. The method of claim 1, wherein the method further comprises:
    providing access to the medical data from the third-party database to a user accessing the primary medical record for the patient maintained by the healthcare cloud computing platform.

7. The method of claim 1, wherein
the medical data for the medical concept is converted to the second plurality of medical properties using a defined standard.

8. The method of claim 7, wherein
the second plurality of medical properties includes name identifiers, medical coding, text data, date of onset, date of documentation, condition type, and diagnosis coding.

9. The method of claim 1, wherein
the third-party database is one of a health information exchange, immunization registry, governmental healthcare registry, pharmaceutical registry, and/or third-party electronic medical record provider.

10. The method of claim 1, wherein
the medical concept includes one or more of: a healthcare organization, practitioner, encounters, problems, encounter diagnosis, allergies, medications, immunizations, clinical notes, pathology documents, cardiology documents, radiology documents, and microbiology documents.

11. The method of claim 1, wherein
the primary medical record is a longitudinal patient record having data from multiple third-party databases.

12. The method of claim 1, wherein
the first plurality of medical properties comprises a third-party database identifier.

13. The method of claim 12, further comprising:
matching the third-party database identified in the medical data to a known third party by the healthcare cloud computing platform.

14. The method of claim 1, wherein the state machine:
creates, during a record retrieval state of the state machine, (1) a first record retrieval queue for the first medical record and a (2) a second record retrieval queue for the second medical record;
normalizes the first plurality of medical properties and the second plurality of medical properties during a normalization state of the state machine;
maps the medical data to a primary medical record in the healthcare cloud computing platform based on the medical data and the primary medical record being associated with a same patient identifier during a patient lookup state; and
evaluates the first medical record and the second medical record by accessing deduplication rules during an organization lookup state; wherein
the record retrieval state is completed before the normalization state, the normalization state is completed before the patient lookup state, and the patient lookup state is completed before the organization lookup state.

15. The method of claim 1, wherein ranking the first medical record and the second medical record to determine a higher-ranking medical record and a lower-ranking medical record comprises:
evaluating an onset date and time rule for a medical concept;
evaluating a clinical status rule for the medical concept;
evaluating a verification status rule for the medical concept; and
storing the onset date and time, clinical status, and verification status of the higher-ranking medical record and the lower-ranking medical record in the provenance module.

16. The method of claim 15, comprising:
multiplying a number of occurrences of the medical property by a weighting factor; wherein the onset date and time rule comprises criteria based on an age of a medical record;
the clinical status rule provides a weighted criteria based on a status selection, the status selection being selected from: resolved, inactive, active, and null;
the verification status rule provides a weighted criteria based on a status selection, the status selection being selected from: entered in error, refuted, confirmed, unconfirmed, and null.

17. The method of claim 1, comprising:
identifying higher-ranking medical record as new;
posting the higher-ranking medical record to the primary record;
staging the higher-ranking medical record for a clinical review; and
writing the higher-ranking medical record into the primary record based on completion of the clinical review.

18. A computer healthcare system, comprising:
one or more hardware processors configured by machine-readable instructions to:
load medical data from a third-party database into a healthcare cloud computing platform, the medical data comprising a first medical record and a second medical record;
identify a medical concept included in the medical data, wherein the medical concept includes a first plurality of medical properties in the first medical record and a second plurality of medical properties in the second medical record;
transform the medical data using a state machine having a state machine definition for the medical concept, to result in transformed medical data, by:
providing the medical data to the state machine;
determining a normalized plurality of medical properties for the medical concept according to the state machine definition;
normalizing the first plurality of medical properties and the second plurality of medical properties according to the state machine definition to generate a first normalized plurality of medical properties for the first medical record and a second normalized plurality of medical properties for the second medical record;
mapping the transformed medical data to a primary medical record in the healthcare cloud computing platform based on the transformed medical data and the primary medical record being associated with a same patient identifier;
evaluate the first medical record and the second medical record by accessing deduplication rules for the cloud computing platform to determine if the first medical record and the second medical record satisfy a rule set for the medical concept;
if the first medical record and the second medical record satisfy the rule set:
determine whether one of the first medical record and the second medical record is in the primary record;
if the first medical record is in the primary record and the second medical record is not in the primary record: store the second medical record in a provenance module;
if the first medical record and the second medical record are not in the primary record:
rank the first medical record and the second medical record to determine a higher-ranking medical record and a lower-ranking medical record;

write the higher-ranking medical record into the primary medical record; and write the lower-ranking medical record into the provenance module;

if the first medical record and the second medical record do not satisfy the rule set:

write data from the first medical record and the second medical record that is not stored in the primary medical record into the primary medical record; and store the determination that the first medical record and the second medical record do not satisfy the rule set in the provenance module.

19. A non-transient computer-readable storage medium having instructions embodied thereon, the instructions being executable by one or more processors to perform a method comprising:

loading medical data from a third-party database into a healthcare cloud computing platform, the medical data comprising a first medical record and a second medical record;

identifying a medical concept included in the medical data, wherein the medical concept includes a first plurality of medical properties in the first medical record and a second plurality of medical properties in the second medical record;

transforming the medical data using a state machine having a state machine definition for the medical concept, to result in transformed medical data, by:

providing the medical data to the state machine;

determining a normalized plurality of medical properties for the medical concept according to the state machine definition; and normalizing the first plurality of medical properties and the second plurality of medical properties according to the state machine definition to generate a first normalized plurality of medical properties for the first medical record and a second normalized plurality of medical properties for the second medical record;

mapping the transformed medical data to a primary medical record in the healthcare cloud computing platform based on the transformed medical data and the primary medical record being associated with a same patient identifier;

evaluating the first medical record and the second medical record by accessing deduplication rules for the cloud computing platform to determine if the first medical record and the second medical record satisfy a rule set for the medical concept;

if the first medical record and the second medical record satisfy the rule set:

determining whether one of the first medical record and the second medical record is in the primary record;

if the first medical record is in the primary record and the second medical record is not in the primary record: storing the second medical record in a provenance module;

if the first medical record and the second medical record are not in the primary record:

ranking the first medical record and the second medical record to determine a higher-ranking medical record and a lower-ranking medical record;

writing the higher-ranking medical record into the primary medical record; and writing the lower-ranking medical record into the provenance module;

if the first medical record and the second medical record do not satisfy the rule set:

writing data from the first medical record and the second medical record that is not stored in the primary medical record into the primary medical record; and storing the determination that the first medical record and the second medical record do not satisfy the rule set in the provenance module.

20. The medium of claim 19, wherein:

a plurality of reads of medical data are ranked according to a time rule, a clinical status rule, and a verification status rule; and the method comprises transforming a property of the primary medical record based a result of the ranking.

* * * * *